United States Patent
Fan et al.

(10) Patent No.: US 8,184,775 B1
(45) Date of Patent: May 22, 2012

(54) DYNAMIC COLLIMATOR FOR WIDE COVERAGE AND LOW DOSE CARDIAC CT IMAGING

(75) Inventors: Jiahua Fan, Waukesha, WI (US); Roy-Arnulf Helge Nilsen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 18 days.

(21) Appl. No.: 12/915,111

(22) Filed: Oct. 29, 2010

(51) Int. Cl.
*G21K 1/02* (2006.01)

(52) U.S. Cl. .................. 378/147; 378/4; 378/8

(58) Field of Classification Search .......... 378/4, 8, 378/145
See application file for complete search history.

(56) References Cited

U.S. PATENT DOCUMENTS

| | | | | |
|---|---|---|---|---|
| 4,200,800 A | * | 4/1980 | Swift | 378/10 |
| 5,615,279 A | * | 3/1997 | Yoshioka et al. | 382/131 |
| 7,953,208 B2 | * | 5/2011 | Kuehn et al. | 378/151 |
| 2004/0223586 A1 | * | 11/2004 | He et al. | 378/86 |

* cited by examiner

*Primary Examiner* — Alexander H Taningco
(74) *Attorney, Agent, or Firm* — Ziolkowski Patent Solutions Group, SC (57) ABSTRACT

A CT scanner comprising a dynamic collimator disposed near an x-ray source and a controller configured to rotate the x-ray source about a subject, wherein imaging data is acquired from a single rotation of the x-ray source, the single rotation being divided into a first half-scan and a second half-scan. The controller is further configured to position the dynamic collimator after acquiring image data from one of the first half-scan and the second half-scan and simultaneous to commencement of acquiring image data from the other of the first half-scan and the second half-scan to obstruct a central portion of an x-ray beam emitted by the x-ray source during one of the first half-scan and the second half-scan. The CT scanner is further configured to reconstruct a CT image using the first set of imaging data and the second set of imaging data.

20 Claims, 7 Drawing Sheets

DYNAMIC COLLIMATOR FOR WIDE COVERAGE AND LOW DOSE CARDIAC CT IMAGING

BACKGROUND OF THE INVENTION

Embodiments of the invention relate generally to diagnostic imaging and, more particularly, to a method and apparatus of computed tomography (CT) imaging capable of having high temporal resolution, reduced image artifacts due to missing data and longitudinal truncation, and reduced radiation dose.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

One of the key modern applications for CT imaging is its use in cardiac imaging. However, cardiac imaging techniques such as coronary CT angiography pose unique technical challenges, one of which is the need for high temporal resolution to avoid motion artifacts in the image. One way to achieve such high temporal resolution is to use wide-coverage multi-detector-row CT (MDCT) systems to scan the entire heart region within one gantry rotation. Here, the wide coverage refers to the x-ray beam coverage in the longitudinal direction, which can cover the majority of the human's heart within one axial rotation. Typically, only data from roughly half of the scan is utilized for image reconstruction to maintain the temporal resolution. Unfortunately, however, such cardiac half-scan imaging methods face severe missing data and longitudinal truncation issues when the large x-ray cone beam angle is large. The cone beam artifacts caused by this cardiac half-scan method are easily observed in the reconstructed images and greatly deteriorate the image quality.

In order to mitigate the missing data and longitudinal truncation problems associated with the cardiac half-scan technique described above, the use of wide-coverage, full-scan cardiac imaging (albeit using a half-scan reconstruction method) is one solution. This wide-coverage, full-scan cardiac imaging offers a way to maintain temporal resolution while alleviating the missing data and longitudinal truncation problems associated with half-scan imaging. However, full-scan cardiac imaging imposes a larger radiation dose on the subject as compared to half-scan cardiac imaging. In fact, the radiation dose in full-scan cardiac imaging represents a 50 percent (or greater) increase in radiation dose over half-scan cardiac imaging. With every effort made to minimize the radiation dose and scan time to which the patient is subjected, conventional full-scan cardiac imaging is less than ideal.

Therefore, it would be desirable to design an apparatus and method for CT imaging capable of having high temporal resolution, reduced image artifacts due to missing data and longitudinal truncation, and reduced radiation dose.

BRIEF DESCRIPTION OF THE INVENTION

An embodiment of the invention is directed to a computed tomography (CT) scanner comprising a gantry having an opening therein to receive a subject to be scanned, an x-ray source disposed within the gantry and configured to project a cone beam of x-rays at the subject during CT data acquisition, and a detector array configured to detect x-rays passing through the subject. The CT scanner further comprises a dynamic collimator disposed near the x-ray source and a controller configured to rotate the x-ray source about the subject, wherein a single rotation of the x-ray source is divided into a first half-scan and a second half-scan, acquire a first set of imaging data during the first half-scan, and acquire a second set of imaging data during the second half-scan. The controller is further configured to position the dynamic collimator after acquiring image data from one of the first half-scan and the second half-scan and simultaneous to commencement of acquiring image data from the other of the first half-scan and the second half-scan, wherein the dynamic collimator is configured to obstruct a central portion of an x-ray beam emitted by the x-ray source during one of the first half-scan and the second half-scan, and reconstruct a CT image using the first set of imaging data and the second set of imaging data.

Another embodiment of the invention is directed to a method of cardiac CT imaging, the method comprising rotating an x-ray source through a series of projection angles about a scan subject along an annular path of rotation, wherein a single rotation of the x-ray source is divided into a first half-scan and a second half-scan, acquiring a first set of imaging data from the first half-scan, and acquiring a second set of imaging data from the second half-scan. The method further comprises deploying a collimator after completion of image data acquisition from one of the first half-scan and the second half-scan and simultaneous to commencement of image data acquisition from the other of the first half-scan and the second half-scan to block a central portion of an x-ray beam emitted by the x-ray source during one of the first half-scan and the second half-scan, and reconstructing a CT image using the first set of imaging data and the second set of imaging data.

Another embodiment of the invention is directed to a CT imaging system comprising a rotatable gantry having an opening therein to receive a subject to be scanned, an x-ray source disposed within the rotatable gantry and configured to project a beam of x-rays at the subject during CT data acquisition, and a collimator disposed near the x-ray source, wherein the collimator is configured to be moveably positioned into the path of the projected beam of x-rays. The CT imaging system further comprises a computer programmed to fully rotate the x-ray source about the subject, wherein the rotation of the x-ray source is divided into a first half-scan and a second half-scan, acquire a first set of imaging data from the first half-scan, and acquire a second set of imaging data from the second half-scan. The computer is further programmed to moveably position the collimator to block a central portion of an x-ray beam emitted by the x-ray source after acquisition of imaging data from one of the first half-scan and the second half-scan, simultaneous to commencement of commencement of acquisition of imaging data from the other of the first half-scan and the second-half scan, and during the entirety of acquisition of imaging data from the other of the first half-scan and the second half-scan, and reconstruct a CT image using the first set of imaging data and the second set of imaging data.

Various other features and advantages will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the invention is described with respect to a wide-coverage multi-detector-row computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
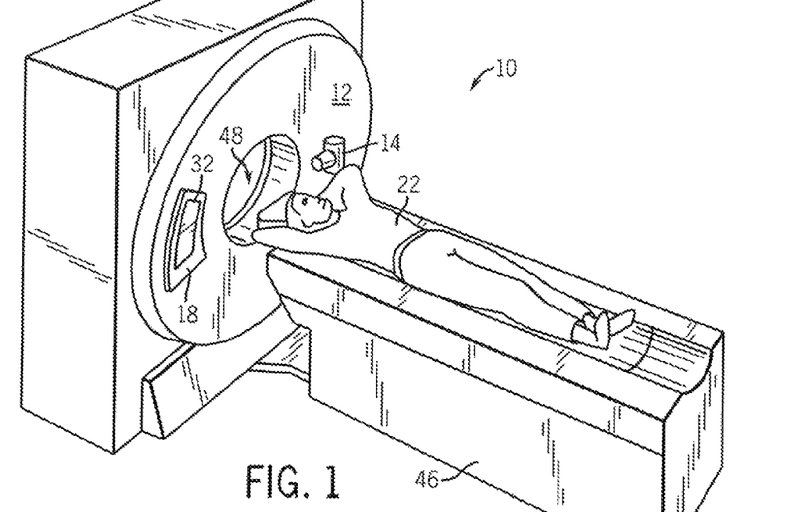
FIG. 1 is a pictorial view of a CT imaging system.
Figure 2:
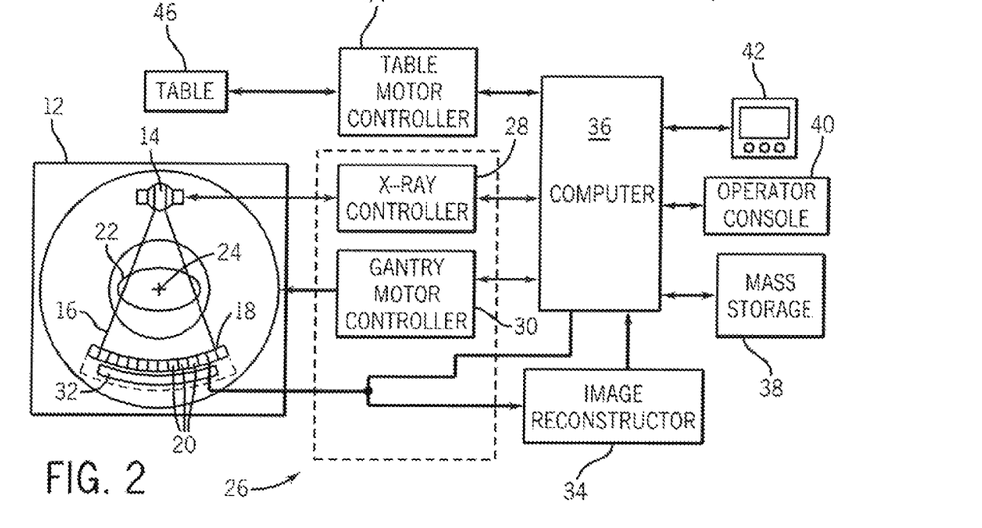
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly or post patient collimation 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
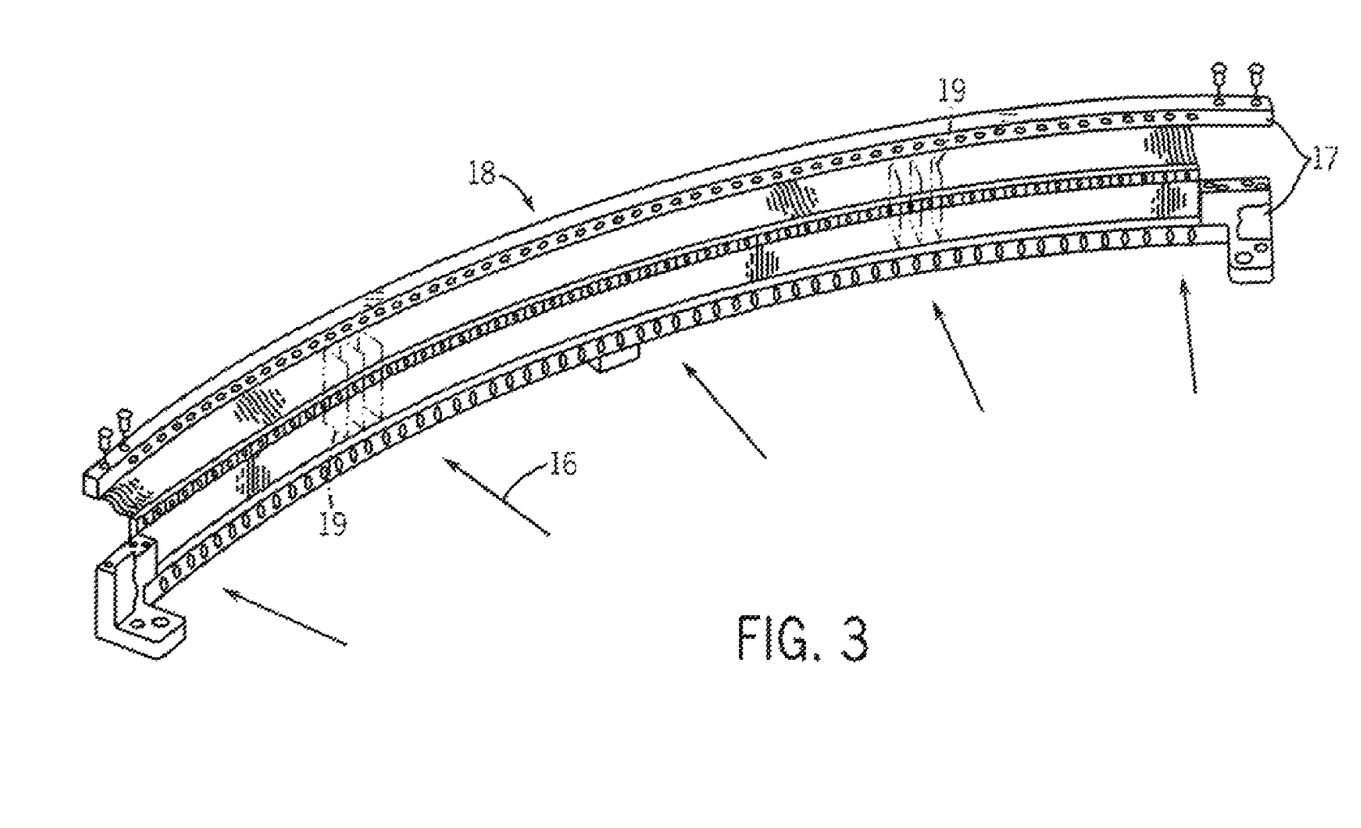
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12. To achieve wide-coverage in longitudinal direction to cover the whole human heart in one rotation, typically more than 64 rows of detectors are required. The number of detector rows required is the function of the coverage required and the detector row width.

Figure 4:
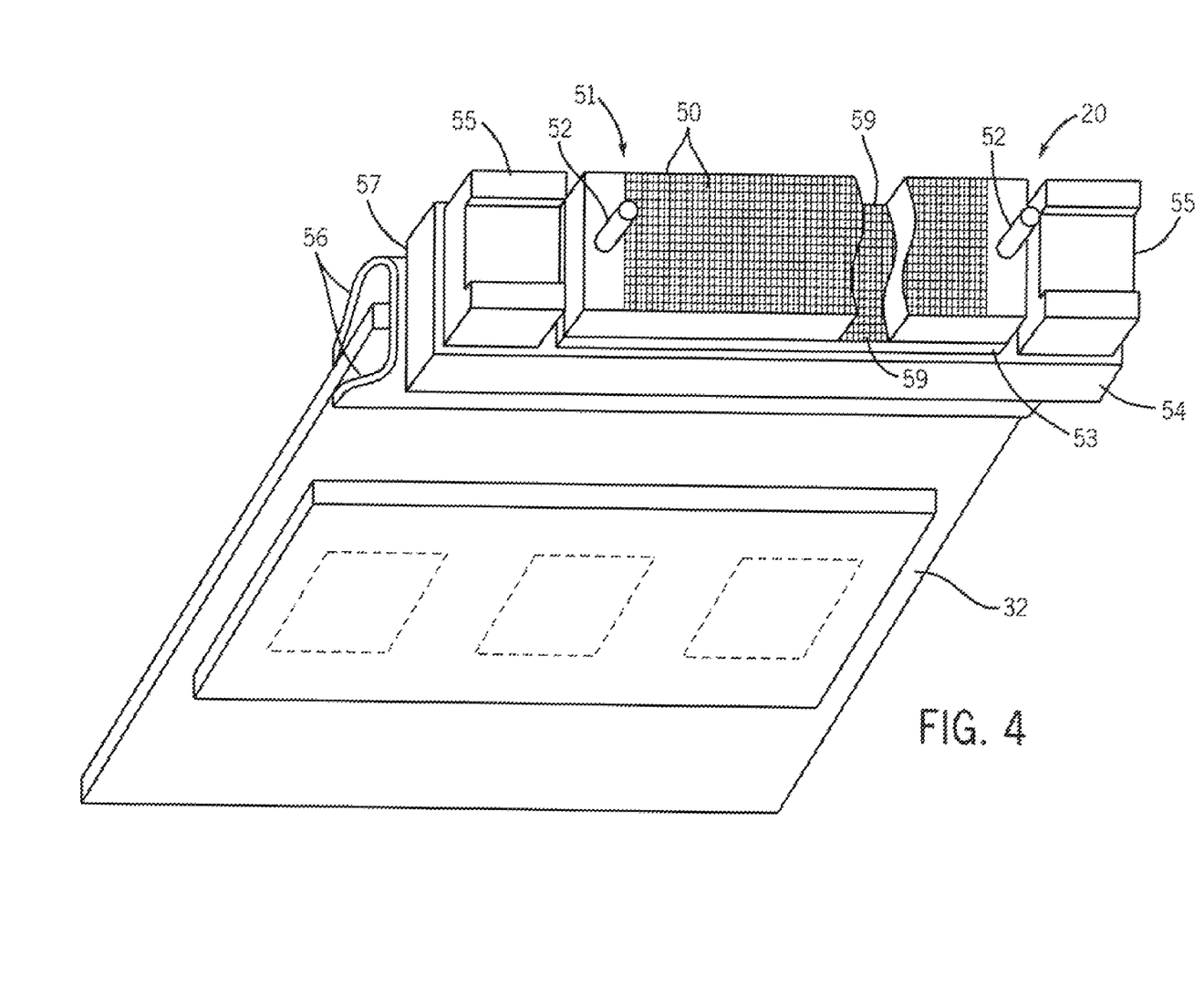
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As discussed above, one of the key modern applications of computed tomography is its use in cardiac imaging. Due to rapid and near-constant cardiac motion, high temporal acquisition speed is used in cardiac CT imaging to avoid motion artifacts in the reconstructed images. To achieve such high temporal resolution, various advanced acquisition techniques have been developed for cardiac imaging, including fast gantry rotation speed, wide longitudinal detector coverage, multiple x-ray sources, etc. Specifically referring to the wide longitudinal detector approach, it is expected that one single axial rotation of the x-ray source about the subject will enable imaging of the whole heart for the majority of the patient population.

Conventionally, cardiac imaging has been performed using a half-scan acquisition mode, which allows for the imaging data needed to reconstruct an image to be acquired from essentially half of the full gantry rotation. However, due to the large cone beam angle present in the wide longitudinal detector approach, severe cone beam artifacts may be present in images generated using the half-scan acquisition mode. Utilization of a full-scan acquisition mode may alleviate the cone beam artifacts present in the image, but it comes at the cost of added radiation dose on the subject.

Figure 5:
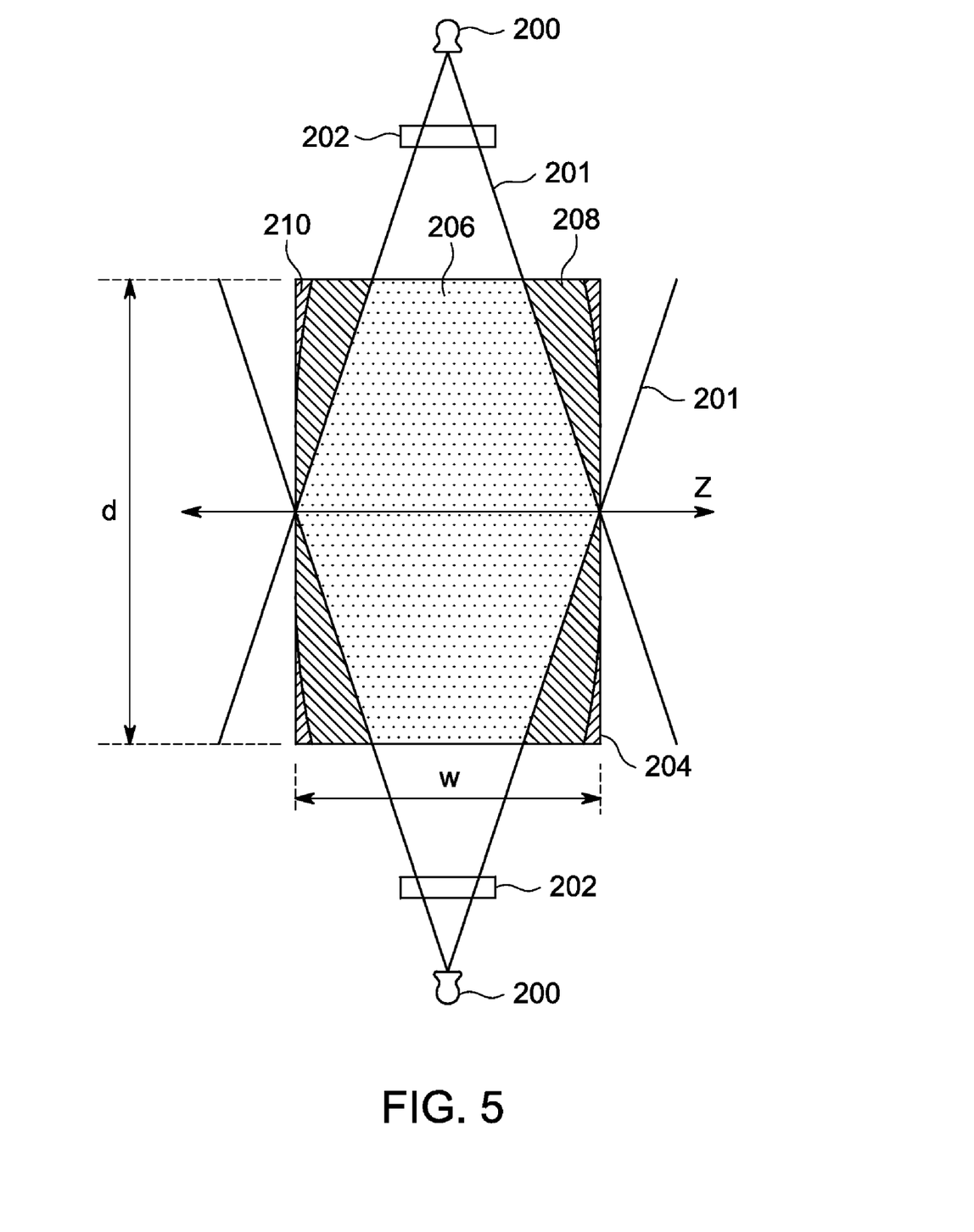
FIG. 5 is a schematic representation of a first half-scan of a wide-longitudinal detector approach to cardiac CT imaging in accordance with an embodiment of the invention.

Referring to FIG. 5, a schematic representation of the wide-longitudinal detector approach to cardiac CT imaging described above is shown. FIG. 5 represents a first half-scan acquisition in accordance with an embodiment of the present invention, as will be described below.

An x-ray source 200 emits a cone-shaped beam of x-rays 201 through bowtie filter 202, which absorbs low energy photons emitted by x-ray source 200 prior to them reaching an object to be scanned. Both x-ray source 200 and bowtie filter 202 rotate axially about the Z-axis of an imaging volume 204. While FIG. 5 shows x-ray source 200 and bowtie filter 202 rotated at only 180-degrees about the Z-axis, this is simply to illustrate the coverage of the cone-shaped beam 201 throughout a scan, and it is to be understood that x-ray source 200 and bowtie filter 202 are capable of a 360-degree rotation about imaging volume 204.

In cardiac CT imaging, imaging volume 204 represents an entire heart region and is the region that is intended to be reconstructed after a single rotation of x-ray source 200 and bowtie filter 202 about the Z-axis. In the example shown in FIG. 5, imaging volume 204 has dimensions in the longitudinal direction of 160 mm (w=160 mm) and an overall diameter of 250 mm (d=250 mm), but it is to be understood that imaging volume 204 is not limited to such dimensions. Furthermore, the distance from x-ray source 200 to the Z-axis in FIG. 5 is 610 mm, but it is to be understood that this distance is not limited to such dimensions, as well.

For a full-scan acquisition of imaging volume 204, x-ray source 200 may be rotated a full axial rotation (i.e., 360-degrees) about imaging volume 204, and imaging data from this full-scan is utilized to reconstruct an image representing imaging volume 204. After imaging data is acquired during a first half-scan (i.e., the first 180-degrees-plus-fan-angle of the full axial rotation), imaging data having complimentary projection angles to that of the first half-scan are acquired during a second half-scan (i.e., the second 180-degree segment of full axial rotation). Thus, full-scan acquisition provides for the greatest range of data to be used in image reconstruction, which is useful in reconstructing images having reduced artifacts. For example, referring to FIG. 5, a full-scan acquisition allows for full 360-degree scan coverage at region 206 of imaging volume 204, greater than 180-degree scan coverage at region 208, and less than 180-degree scan coverage at region 210. For a reconstructed image to have little-to-no cone beam artifacts, at least 180-degrees of scan coverage is desired, and such scan coverage is substantially obtained using full-scan acquisition. In fact, using the example set forth in FIG. 5, more than 98% of coverage data is provided via a full-scan acquisition, with only minimal region 210 providing less than 180 degrees of scan coverage under these conditions.

While a full-scan acquisition successfully enables images having minimal cone beam artifacts to be acquired, such a full-scan acquisition also subjects the object to be scanned to undesirable additional radiation dosage. As an alternative, a half-scan acquisition approach may be utilized to reduce radiation dose, but such an approach on its own leads to substantially less coverage data being available for image reconstruction as compared with a full-scan acquisition. As stated above, at least 180-degrees of scan coverage is desired for image reconstruction. Using only a half-scan acquisition, much less data coverage is possible, and thus substantial portions of imaging volume 204 would contain insufficient data for image reconstruction. For example, referring again to FIG. 5, region 206 of imaging volume 204 will have greater than 180-degrees of scan coverage using the half-scan acquisition approach, but region 208 will have less than 180-degrees of scan coverage, and region 210 will have much less than 180-degrees of scan coverage, resulting in approximately 86% of overall coverage data (as compared to more than 98% of coverage data using full-scan acquisition). The lack of scan coverage in conventional half-scan acquisition alone results in undesirable cone beam artifacts, and thus the half-scan acquisition approach is not attractive for use in wide-coverage cardiac imaging when cone beam artifacts are the main concern.

Therefore, while FIG. 5 illustrates a first half-scan acquisition in accordance with an embodiment of the invention, a second half-scan acquisition is desired to enable acquisition of sufficient data for low-artifact image reconstruction, yet minimize additional radiation dose to which the scanned object is subjected. Embodiments of the invention achieve such an image data acquisition method using respective first and second half-scan acquisitions, as will be described further herein with respect to FIG. 6.

Figure 6:
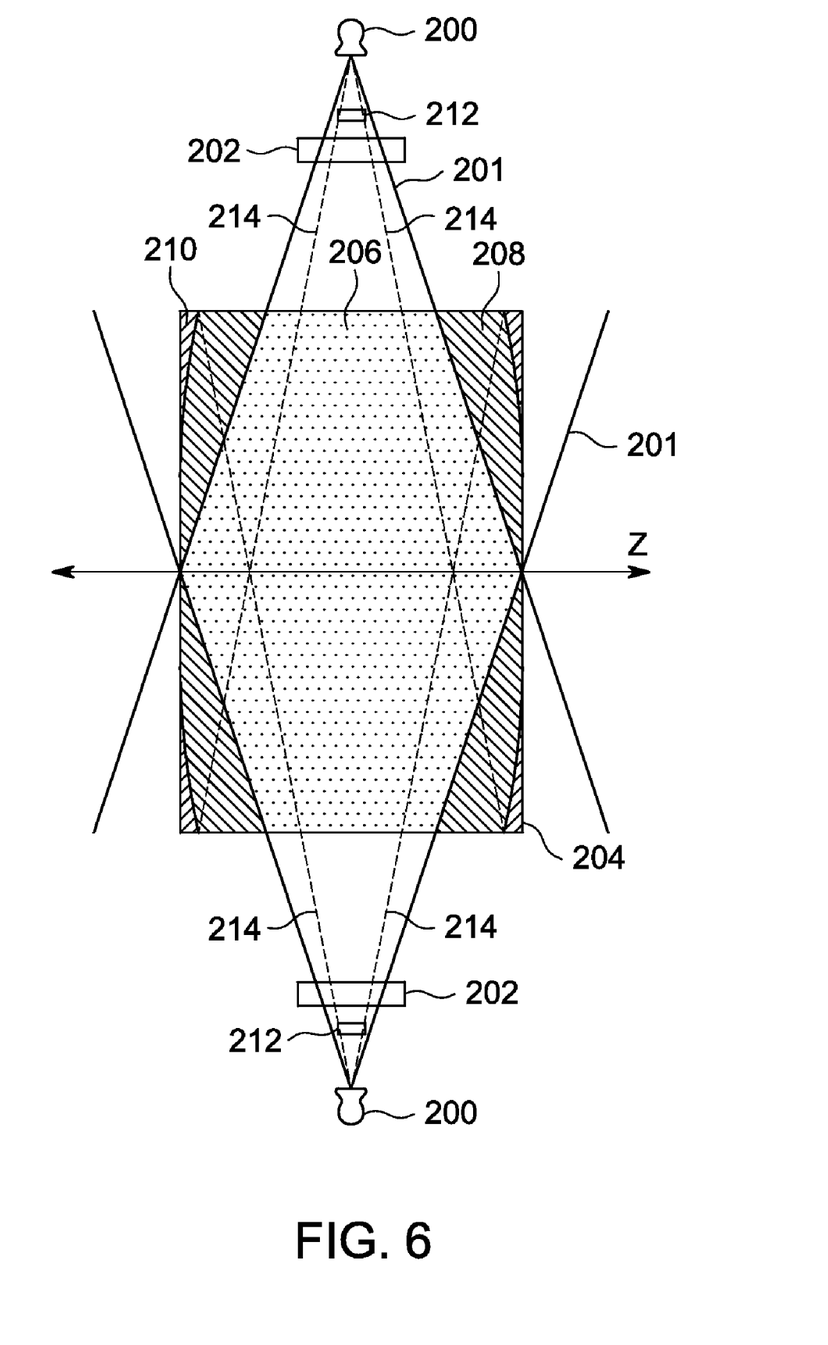
FIG. 6 is a schematic representation of a second half-scan of a wide-longitudinal detector approach to cardiac CT imaging in accordance with an embodiment of the invention.

Referring to FIG. 6, a schematic representation of a second half-scan acquisition in accordance with embodiments of the invention is shown. For the sake of consistency and ease of understanding, common elements between FIG. 5 and FIG. 6 share common reference numbers, and the purpose or meaning of each common element will not be reiterated herein.

As described above with respect to FIG. 5, image data from a first half-scan is acquired by axially rotating x-ray source 200 and bowtie filter 202 about the Z-axis of imaging volume 204, and imaging data is continuously acquired during this first half-scan. The first half-scan constitutes a 180-degree rotation about the Z-axis, along with the fan angle of the x-ray beam. Sufficient image data is acquired for region 206 during this first half-scan, as greater than 180-degrees of scan coverage is obtained in region 206. However, insufficient data is acquired in region 208 and region 210 from the first half-scan alone, and thus full-scan acquisition is more attractive for effective image reconstruction of the entirety of imaging volume 204.

Thus, after image data acquisition during the first half-scan, x-ray source 200 enters the second 180-degrees of axial rotation about imaging volume 204, referred to as the second half-scan. However, simultaneous to commencement of image data acquisition in the second half-scan, a dynamic collimator 212 is moveably positioned between x-ray source 200 and bowtie filter 202 so as to effectively block a central portion of the x-ray beam emitted from x-ray source 200. In this way, dynamic collimator 212 obstructs much of the x-ray beam emitted from the x-ray source 200, but allows outer portions of the x-ray beam (that is, portions of the x-ray beam outside of lines 214) to impinge on the scanned object during the second half-scan. Redundant and unnecessary image data from region 206 that was already acquired during the first half-scan is not acquired during the second half-scan, while image data from undersampled region 208 and region 210 is still acquired during the second half-scan, thereby enabling at least 180-degrees of data coverage to be acquired for most of imaging volume 204. Upon acquisition of image data from both the first half-scan and the second half-scan, a CT image is reconstructed.

The CT imaging technique described above with respect to FIG. 5 and FIG. 6 not only enables sufficient data coverage to be acquired, but also substantially reduces the potential radiation dose to which the scanned object is subjected. Furthermore, when this technique is implemented for cardiac CT imaging with certain gantry rotation speed, the entire full-scan acquisition can be completed within a single heartbeat, thereby achieving the high temporal resolution necessary to avoid motion artifacts.

Dynamic collimator 212 is preferably formed of a high attenuation material (e.g., tungsten), which enables it to effectively block a substantial portion of the x-ray beam emitted by x-ray source 200. While the term "collimator" is used, dynamic collimator 212 does not shape the x-ray beam in the conventional sense, but instead blocks a substantial central portion (i.e., 80 percent) of the x-ray beam, while allowing outer portions of the x-ray beam to impinge upon the scanned object. Unlike conventional collimators used in CT imaging, dynamic collimator 212 is also formed as a single unit. Furthermore, dynamic collimator 212 may be moveably positioned between x-ray source 200 and bowtie 202 after the first half-scan and simultaneous to commencement of the second half-scan using any appropriate actuation means. However, while the example set forth above specifies that dynamic collimator 212 is deployed during the second half-scan, the invention is not limited as such. That is, dynamic collimator 212 could be positioned to block a portion of the x-ray beam during the first half-scan and not be positioned to block a portion of the x-ray beam during the second half-scan. Furthermore, the dynamic collimator 212 could be positioned to block a portion of the x-ray beam during any period of the full scan.

Without use of dynamic collimator 212 during the second half-scan, the radiation dose could be, for example, more than 50% higher during full-scan acquisition than simply taking a half-scan acquisition for the same coverage. However, using dynamic collimator 212 to block, for example, an 80% portion of the x-ray beam during the second half-scan ensures that the object being imaged is covered uniformly by at least 180 degree sampling. This approach amounts to a radiation dose reduction of approximately 30% over conventional full-scan acquisition. Such a substantial reduction in radiation dose, when coupled high temporal resolution and reduced cone beam artifacts, make the wide coverage full-scan acquisition technique described with respect to the invention an attractive option for cardiac CT imaging.

Figure 7:
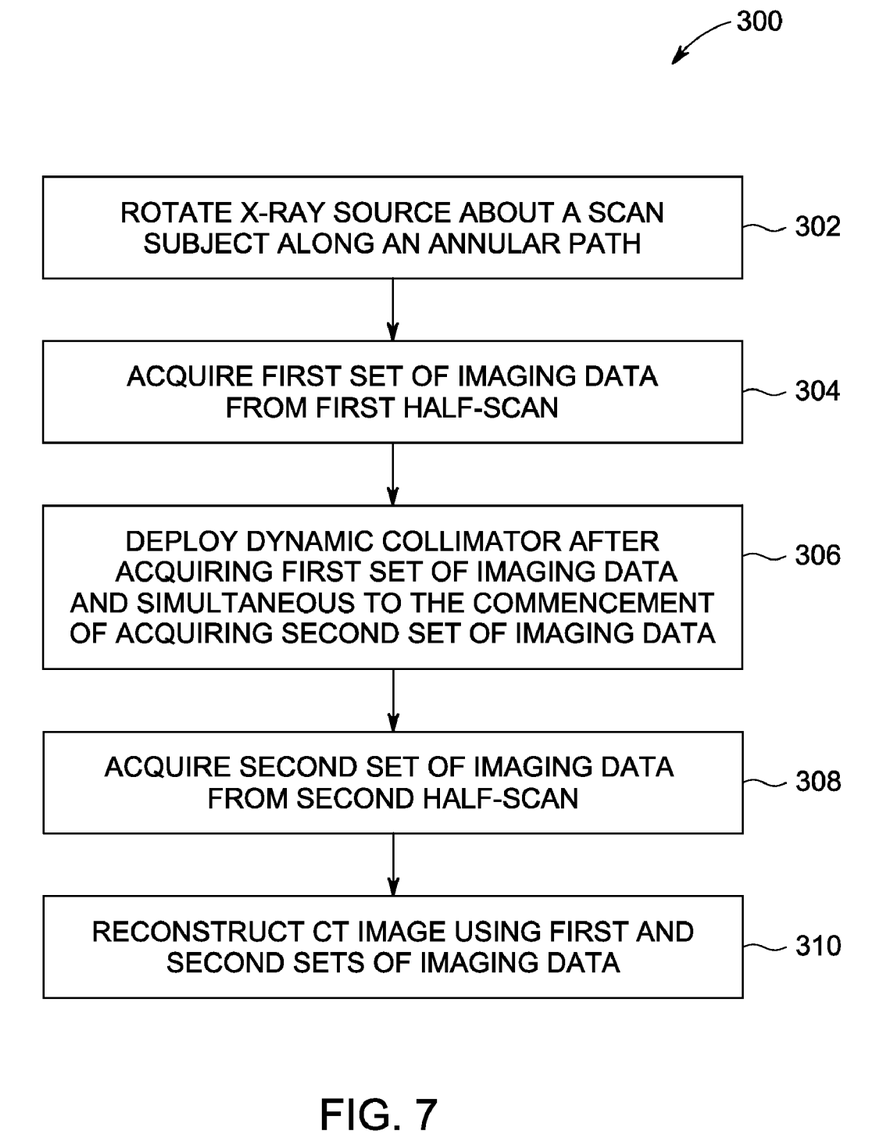
FIG. 7 is a flowchart showing a method of CT imaging in accordance with an embodiment of the invention.

Referring now to FIG. 7, a method of CT imaging 300 in accordance with an embodiment of the invention is shown. Method 300 begins with rotating an x-ray source about a scan subject (e.g., a patient) along an annular path at block 302. At block 304, a first set of imaging data is acquired from the first half-scan from the x-ray source. Next, at block 306, a dynamic collimator is deployed after completion of the acquisition of imaging data during the first half-scan and simultaneous to commencement of imaging data acquisition from a second half scan. As described above, the dynamic collimator is configured to block a substantial portion of the x-ray beam emitted by the x-ray source during the second half-scan. At block 308, a second set of imaging data is acquired from the second half-scan, thereby completing a full-scan acquisition of image data. Finally, at block 310, a CT image is reconstructed using the acquired first and second sets of imaging data.

Figure 8:
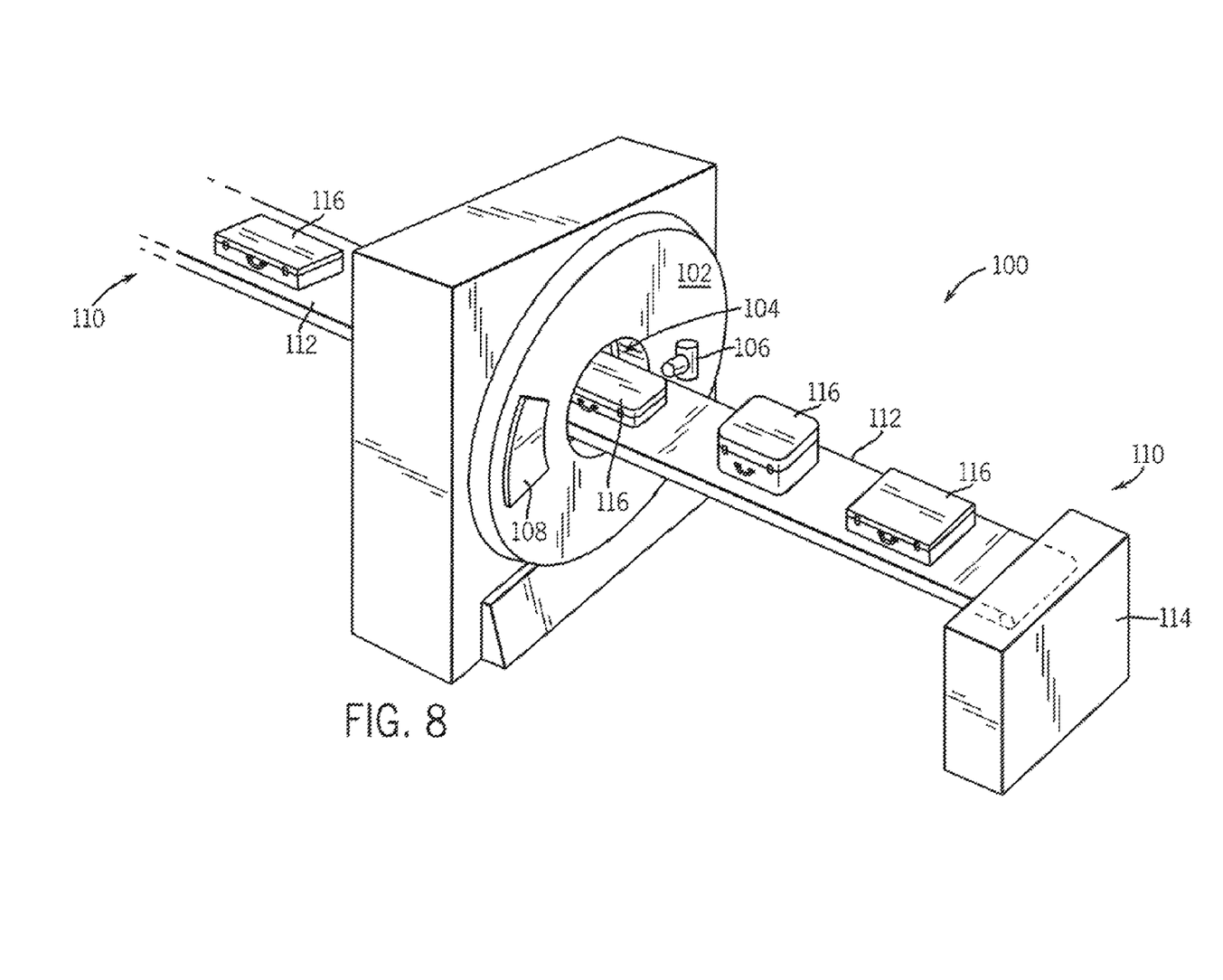
FIG. 8 is a pictorial view of a CT system for use with a non-invasive package inspection system.

While the above examples pertain specifically to cardiac CT imaging, the invention is not limited as such. The invention may be applied to other forms of CT imaging, particularly those in which reduced or limited radiation dose is desired, including neuro studies and pediatric scans, Referring now to FIG. 8, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

A technical contribution for the disclosed method and apparatus is that is provides for a computer implemented to perform a method of computed tomography (CT) imaging capable of having high temporal resolution, reduced image artifacts due to missing data and longitudinal truncation, and reduced radiation dose.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Accordingly, an embodiment of the invention is directed to a computed tomography (CT) scanner comprising a gantry having an opening therein to receive a subject to be scanned, an x-ray source disposed within the gantry and configured to project a cone beam of x-rays at the subject during CT data acquisition, and a detector array configured to detect x-rays passing through the subject. The CT scanner further comprises a dynamic collimator disposed near the x-ray source and a controller configured to rotate the x-ray source about the subject, wherein a single rotation of the x-ray source is divided into a first half-scan and a second half-scan, acquire a first set of imaging data during the first half-scan, and acquire a second set of imaging data during the second half-scan. The controller is further configured to position the dynamic collimator after acquiring image data from one of the first half-scan and the second half-scan and simultaneous to commencement of acquiring image data from the other of the first half-scan and the second half-scan, wherein the dynamic collimator is configured to obstruct a central portion of an x-ray beam emitted by the x-ray source during one of the first half-scan and the second half-scan, and reconstruct a CT image using the first set of imaging data and the second set of imaging data.

Another embodiment of the invention is directed to a method of cardiac CT imaging, the method comprising rotating an x-ray source through a series of projection angles about a scan subject along an annular path of rotation, wherein a single rotation of the x-ray source is divided into a first half-scan and a second half-scan, acquiring a first set of imaging data from the first half-scan, and acquiring a second set of imaging data from the second half-scan. The method further comprises deploying a collimator after completion of image data acquisition from one of the first half-scan and the second half-scan and simultaneous to commencement of image data acquisition from the other of the first half-scan and the second half-scan to block a central portion of an x-ray beam emitted by the x-ray source during one of the first half-scan and the second half-scan, and reconstructing a CT image using the first set of imaging data and the second set of imaging data.

Yet another embodiment of the invention is directed to a CT imaging system comprising a rotatable gantry having an opening therein to receive a subject to be scanned, an x-ray source disposed within the rotatable gantry and configured to project a beam of x-rays at the subject during CT data acquisition, and a collimator disposed near the x-ray source, wherein the collimator is configured to be moveably positioned into the path of the projected beam of x-rays. The CT imaging system further comprises a computer programmed to fully rotate the x-ray source about the subject, wherein the rotation of the x-ray source is divided into a first half-scan and a second half-scan, acquire a first set of imaging data from the first half-scan, and acquire a second set of imaging data from the second half-scan. The computer is further programmed to moveably position the collimator to block a central portion of an x-ray beam emitted by the x-ray source after acquisition of imaging data from one of the first half-scan and the second half-scan, at commencement of acquisition of imaging data from the other of the first half-scan and the second-half scan, and during the entirety of acquisition of imaging data from the other of the first half-scan and the second half-scan, and reconstruct a CT image using the first set of imaging data and the second set of imaging data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) scanner comprising:
    a gantry having an opening therein to receive a subject to be scanned;
    an x-ray source disposed within the gantry and configured to project a cone beam of x-rays at the subject during CT data acquisition;
    a detector array configured to detect x-rays passing through the subject;
    a dynamic collimator disposed near the x-ray source; and
    a controller configured to:
        rotate the x-ray source about the subject, wherein a single rotation of the x-ray source is divided into a first half-scan and a second half-scan;
        acquire a first set of imaging data during the first half-scan;
        acquire a second set of imaging data during the second half-scan;
        position the dynamic collimator after acquiring image data from one of the first half-scan and the second half-scan and simultaneous to the commencement of acquiring image data from the other of the first half-scan and the second half-scan, wherein the dynamic collimator is configured to obstruct a central portion of an x-ray beam emitted by the x-ray source during one of the first half-scan and the second half-scan; and
        reconstruct a CT image using the first set of imaging data and the second set of imaging data.

2. The CT scanner of claim 1 further comprising a bowtie filter disposed near the x-ray source to absorb low-energy photons prior to reaching the subject, wherein the controller is configured to position the dynamic collimator between the x-ray source and the bowtie filter.

3. The CT scanner of claim 1 wherein the dynamic collimator is formed of a material having high x-ray attenuation characteristics.

4. The CT scanner of claim 3 wherein the dynamic collimator is formed of tungsten.

5. The CT scanner of claim 1 wherein the dynamic collimator comprises a single element configured to obstruct a portion of the x-ray beam.

6. The CT scanner of claim 1 wherein the dynamic collimator is positioned a distance from the x-ray source so as to block only a central portion of the x-ray beam emitted by the x-ray source and allow outer portions of the x-ray beam to reach the subject.

7. The CT scanner of claim 1 wherein the dynamic collimator is configured to block 80 percent of the x-ray beam emitted by the x-ray source during the second half-scan.

8. The CT scanner of claim 1 wherein the controller is configured to rotate the x-ray source entirely about the subject within a single heartbeat of the subject.

9. The CT scanner of claim 1 wherein the controller is configured to reconstruct the CT image from the first set of imaging data and the second set of imaging data acquired from a full rotation of the x-ray source about the subject.

10. The CT scanner of claim 1 wherein the detector array is a multi-detector-row array.

11. A method of cardiac CT imaging, the method comprising:
rotating an x-ray source through a series of projection angles about a scan subject along an annular path of rotation, wherein a single rotation of the x-ray source is divided into a first half-scan and a second half-scan;
acquiring a first set of imaging data from the first half-scan;
acquiring a second set of imaging data from the second half-scan;
deploying a collimator after completion of image data acquisition from one of the first half-scan and the second half-scan and simultaneous to the commencement of image data acquisition from the other of the first half-scan and the second half-scan to block a central portion of an x-ray beam emitted by the x-ray source during one of the first half-scan and the second half-scan; and
reconstructing a CT image using the first set of imaging data and the second set of imaging data.

12. The method of claim 11 further comprising defining a complimentary projection angle of the second half-scan for each projection angle of the first half-scan.

13. The method of claim 11 wherein the step of reconstructing a CT image comprises reconstructing an image using the first set of imaging data and the second set of imaging data acquired from a full rotation of the x-ray source about the scan subject.

14. The method of claim 11 further comprising fully rotating the x-ray source about the scan subject within a single heartbeat duration of the scan subject.

15. The method of claim 11 wherein the step of deploying the collimator comprises blocking 80 percent of the x-ray beam emitted by the x-ray source during the second half-scan.

16. A CT imaging system comprising:
a rotatable gantry having an opening therein to receive a subject to be scanned;
an x-ray source disposed within the rotatable gantry and configured to project a beam of x-rays at the subject during CT data acquisition;
a collimator disposed near the x-ray source, wherein the collimator is configured to be moveably positioned into the path of the projected beam of x-rays; and
a computer programmed to:
fully rotate the x-ray source about the subject, wherein the rotation of the x-ray source is divided into a first half-scan and a second half-scan;
acquire a first set of imaging data from the first half-scan;
acquire a second set of imaging data from the second half-scan;
moveably position the collimator to block a central portion of an x-ray beam emitted by the x-ray source after acquisition of imaging data from one of the first half-scan and the second half-scan, at commencement of acquisition of imaging data from the other of the first half-scan and the second-half scan, and during the entirety of acquisition of imaging data from the other of the first half-scan and the second half-scan; and
reconstruct a CT image using the first set of imaging data and the second set of imaging data.

17. The CT system of claim 16 wherein the collimator is formed as a single unit having high x-ray attenuation characteristics.

18. The CT system of claim 16 wherein the computer is further programmed to cause rotation of the gantry at a gantry speed such that the first half-scan and second half-scan occur within a single heartbeat duration.

19. The CT system of claim 16 wherein the computer is further programmed to define the first half-scan and the second half-scan such that an imaging volume of first half-scan partially overlaps the imaging volume of the second half-scan.

20. The CT system of claim 16 wherein the collimator is sized and disposed a distance from the x-ray source such that the collimator blocks only a central portion of the x-ray beam emitted by the x-ray source at the subject during the second half-scan.

* * * * *